United States Patent
Maruhata (10) Patent No.: US 9,365,023 B2
(45) Date of Patent: Jun. 14, 2016

(54) PARTICLE SUPPLYING APPARATUS AND SHEET ARTICLE MANUFACTURING APPARATUS

(75) Inventor: Kazuya Maruhata, Mima-gun (JP)

(73) Assignee: LIVEDO CORPORATION, Shikokuchuo-shi, Ehime (JP)

(*) Notice: Subject to any disclaimer, the term of this patent is extended or adjusted under 35 U.S.C. 154(b) by 254 days.

(21) Appl. No.: 14/129,048

(22) PCT Filed: Jul. 5, 2012

(86) PCT No.: PCT/JP2012/004390
§ 371 (c)(1),
(2), (4) Date: Dec. 23, 2013

(87) PCT Pub. No.: WO2013/008434
PCT Pub. Date: Jan. 17, 2013

(65) Prior Publication Data
US 2014/0144586 A1 May 29, 2014

(30) Foreign Application Priority Data
Jul. 8, 2011 (JP) .................................. 2011-151581

(51) Int. Cl.
*B28B 19/00* (2006.01)
*B29C 65/48* (2006.01)
(Continued)

(52) U.S. Cl.
CPC ........... *B32B 37/24* (2013.01); *A61F 13/15658* (2013.01); *B05C 19/04* (2013.01); *B05C 5/0233* (2013.01); *B05C 5/0245* (2013.01); *B32B 37/20* (2013.01); *B32B 2555/02* (2013.01)

(58) Field of Classification Search
USPC ......... 156/278–280, 390, 547, 548, 553, 555, 156/581, 582
See application file for complete search history.

(56) References Cited

U.S. PATENT DOCUMENTS 4,851,069 A * 7/1989 Packard .............. A61F 13/1565
156/276
4,994,053 A * 2/1991 Lang .................. A61F 13/15634
428/117
(Continued)

FOREIGN PATENT DOCUMENTS

EP 1 621 165 A1 2/2006
EP 1 621 166 A1 2/2006
(Continued)

OTHER PUBLICATIONS

International Search Report dated Oct. 30, 2012 issued in corresponding application No. PCT/JP2012/004390.
(Continued)

*Primary Examiner* — Sing P Chan
(74) *Attorney, Agent, or Firm* — Westerman, Hattori, Daniels & Adrian, LLP (57) ABSTRACT

An absorbent sheet manufacturing apparatus is provided with a cylinder part (21) having a plurality of through-holes (212) arranged in a circumferential direction. The cylinder part (21) is rotated, and therefore particles of high-absorbent resin are sequentially filled into the through-holes (212) from a particle storage space (217) in the cylinder part (21). In a particle supply region (210) of a lower portion of the cylinder part (21), the inner side surface (215) of the cylinder part (21) is covered with an isolation part (25) so that each through-hole (212) filled with particles is isolated from the particle storage space (217). And in this state, particles are ejected from the through-hole (212). As above, only particles filled in each through-hole (212) are ejected, and therefore a desired amount of particles can be easily supplied from the through-hole (212).

16 Claims, 7 Drawing Sheets

(51) Int. Cl.
*B32B 37/24* (2006.01)
*B32B 38/18* (2006.01)
*A61F 13/15* (2006.01)
*B05C 19/04* (2006.01)
B05C 5/02 (2006.01)
B32B 37/20 (2006.01)

(56) References Cited

U.S. PATENT DOCUMENTS

| | | | | |
|---|---|---|---|---|
| 7,744,713 | B2 * | 6/2010 | Blessing | A61F 13/15658 156/196 |
| 8,163,124 | B2 * | 4/2012 | Moriura | A61F 13/15658 156/276 |
| 2006/0278335 | A1 * | 12/2006 | Moriura | A61F 13/15658 156/279 |
| 2009/0056867 | A1 * | 3/2009 | Moriura | A61F 13/15658 156/276 |
| 2014/0099429 | A1 * | 4/2014 | Maruhata | A61F 13/1565 427/8 |
| 2014/0116626 | A1 * | 5/2014 | Maruhata | A61F 13/15658 156/547 |
| 2014/0124143 | A1 * | 5/2014 | Maruhata | A61F 13/15658 156/383 |
| 2014/0138031 | A1 * | 5/2014 | Maruhata | A61F 13/15658 156/390 |
| 2014/0144587 | A1 * | 5/2014 | Maruhata | A61F 13/15658 156/390 |

FOREIGN PATENT DOCUMENTS

| | | |
|---|---|---|
| EP | 1 655 007 A1 | 5/2006 |
| EP | 2 412 346 A1 | 2/2012 |
| EP | 2 444 045 A1 | 4/2012 |
| JP | 2005-59579 A | 3/2005 |
| JP | 2007-130818 A | 5/2007 |
| JP | 2008-507384 A | 3/2008 |
| JP | 2010-246989 A | 11/2010 |
| WO | 2006/014854 A1 | 2/2006 |
| WO | 2006/015138 A1 | 2/2006 |

OTHER PUBLICATIONS

Written Opinion for PCTJP2012/004390, Mailing Date of Oct. 30, 2012.

* cited by examiner

PARTICLE SUPPLYING APPARATUS AND SHEET ARTICLE MANUFACTURING APPARATUS

TECHNICAL FIELD

The present invention relates to a particle supplying apparatus for supplying particles of absorbent material or deodorant material onto a sheet member, and a sheet article manufacturing apparatus comprising the particle supplying apparatus for manufacturing a sheet article for an absorbent article.

BACKGROUND ART

In an absorbent article such as an absorbent pad for light incontinence which is used by being attached on the inside of a disposable diaper, an absorbent sheet is conventionally utilized which is obtained by sandwiching particles of high-absorbent resin between two sheet members formed of non-woven fabric or the like to fix the particles therebetween.

Japanese Patent Application Laid-Open No. 2005-59579 is related to a manufacturing apparatus for manufacturing a sheet-like absorbent body used for a disposable absorbent article. The apparatus is provided with a temporary receiving roller having an outer side surface on which a plurality of concave grooves intermittently arranged in a circumferential direction are formed, a transfer roller for holding a base sheet under the temporary receiving roller to convey the base sheet, a box located above the temporary receiving roller for supplying high-absorbent resin particles into the above plurality of concave grooves, and an arcuate guide member facing the outer side surface of the temporary receiving roller in a region from the box to the transfer roller to hold the high-absorbent resin particles supplied in the plurality of concave grooves. The high-absorbent resin particles held in the plurality of concave grooves in the temporary receiving roller are moved to a lower position by rotation of the temporary receiving roller, to be supplied onto the base sheet on which hot melt adhesive is applied. Then, by bonding a cover sheet on the base sheet with high-absorbent resin particles placed therebetween, the sheet-like absorbent body is formed.

In an apparatus disclosed in International Publication No. WO 2006/14854 (Document 2), a centrifugal roll comprises a central portion of cylindrical form and frustoconical inlet portions located on both sides of the central portion, and the centrifugal roll is provided above a non-woven web. A screen printing roll and a belt are provided around the centrifugal roll. Openings are formed in the screen printing roll, and the belt covers portions of the screen printing roll other than a portion facing the non-woven web. Absorbent gelling material granules supplied in the centrifugal roll are collected to the central portion by centrifugal forces and are discharged from the central portion to the outside, to be supplied onto the non-woven web through the openings of the screen printing roll.

Incidentally, in the apparatus of Document 2, absorbent gelling material granules which have been moved to the central portion along an inner side surface of the centrifugal roll are further moved to the outside from the central portion by centrifugal forces. Thus, it is impossible to store the granules in the central portion of the centrifugal roll, and if the amount of granules discharged from the central portion to the outside is greater than a predetermined amount at a timing, the amount of granules discharged at the next timing is insufficient. In order to keep the granule-discharged amount constant in the apparatus, it is necessary to accurately control the amount of granules supplied to the centrifugal roll per unit time, a rotation speed of the centrifugal roll and the like. However, even if such control is performed, the granule-discharged amount changes due to a variation of particle size of granules or the like, and it is not easy that the amount of granules discharged from the centrifugal roll is kept constant.

SUMMARY OF INVENTION

The present invention is intended for a particle supplying apparatus for supplying particles of absorbent material or deodorant material onto a sheet member. It is an object of the present invention to easily supply a desired amount of particles from each through-hole of a cylinder part in the particle supplying apparatus.

The particle supplying apparatus according to the present invention comprises: a cylinder part which is an generally cylindrical member around a rotation axis along a horizontal direction, a portion of the internal space being a particle storage space which stores particles of absorbent material or deodorant material, the cylinder part having a plurality of through-holes arranged in a circumferential direction and being rotated around the rotation axis so that particles are filled into a through-hole out of the plurality of through-holes which faces particles stored in the particle storage space, to eject particles filled in the through-hole outward at a particle supply region provided in a lower portion thereof; a sheet conveying part for conveying a sheet member in a direction under the particle supply region, the direction being same as a moving direction of an outer side surface of the cylinder part; a cover part which spreads from the particle supply region along an opposite direction of a rotation direction of the cylinder part to cover a portion of the outer side surface of the cylinder part and close an outer end of the through-hole filled with particles; and an isolation part which covers a portion of an inner side surface of the cylinder part to isolate a through-hole in the particle supply region from the particle storage space.

In the present invention, it is possible to easily supply a desired amount of particles from each through-hole of the cylinder part.

According to a preferred embodiment of the present invention, the isolation part has an air supply path for conducting air into a through-hole of the cylinder part at a posterior end portion of the particle supply region in the rotation direction. Therefore, particles can be ejected smoothly from the through-hole. In this case, if the particle supplying apparatus further comprises an air supply part for forcedly supplying air into the air supply path, particles can be ejected more smoothly from the through-hole.

According to another preferred embodiment of the present invention, the particle supplying apparatus further comprises a particle replenishment part for replenishing particles into the particle storage space from one end portion of the cylinder part in an axial direction thereof. This makes it possible to easily perform replenishment of particles into the particle storage space.

The present invention is also intended for a sheet article manufacturing apparatus for manufacturing a sheet article for an absorbent article. The sheet article manufacturing apparatus comprises the above particle supplying apparatus; another sheet conveying part for conveying another sheet member; and a sheet bonding part for placing the another sheet member on the sheet member which has been supplied with particles by the particle supplying apparatus, to bond the another sheet member on the sheet member.

These and other objects, features, aspects and advantages of the present invention will become more apparent from the following detailed description of the present invention when taken in conjunction with the accompanying drawings.

DESCRIPTION OF EMBODIMENTS

Figure 1:
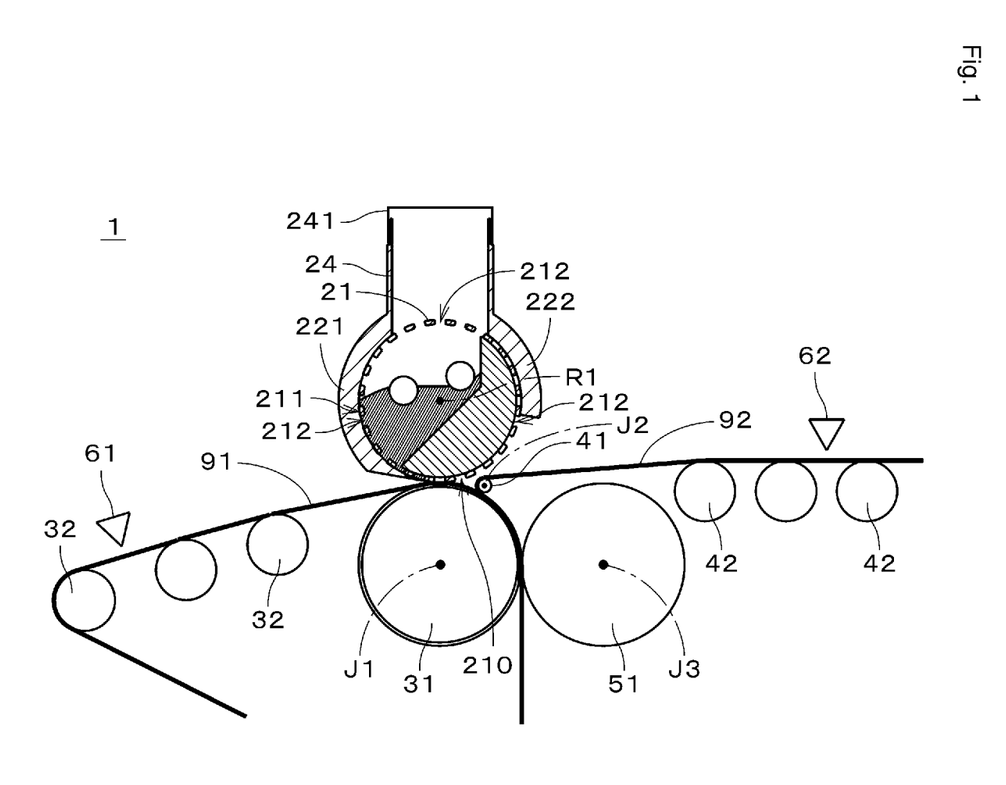
FIG. 1 is a view showing an absorbent sheet manufacturing apparatus in accordance with a first preferred embodiment.

FIG. 1 is a view showing an absorbent sheet manufacturing apparatus 1 in accordance with a first preferred embodiment of the present invention. The absorbent sheet manufacturing apparatus 1 is one sheet article manufacturing apparatus for manufacturing a sheet article for an absorbent article and manufactures absorbent sheets by sandwiching particles of high-absorbent resin such as SAP (Super Absorbent Polymer) between sheet members formed of nonwoven fabric or the like. The absorbent sheet is a sheet article used for an absorbent article such as a disposable diaper or absorbent pad for light incontinence.

The absorbent sheet manufacturing apparatus 1 has a cylinder part 21 which is a generally cylindrical member around (with its center lying on) a rotation axis R1 along (toward) a horizontal direction, a first sheet conveying roller 31 having a generally columnar shape around a first central axis J1 parallel to a direction along the rotation axis R1 (hereinafter, the direction is referred to as an "axial direction"), a second sheet conveying roller 41 having a generally columnar shape around a second central axis J2 parallel to the axial direction, and a bonding roller 51 having a generally columnar shape around a third central axis J3 parallel to the axial direction. The first central axis J1 is positioned right below the rotation axis R1 in the vertical direction. The absorbent sheet manufacturing apparatus 1 also has a plurality of auxiliary rollers 32, 42 each having a generally columnar shape around a central axis parallel to the axial direction, and a first applying part 61 and second applying part 62 each for applying adhesive (in the present embodiment, hot melt adhesive).

The cylinder part 21, the second sheet conveying roller 41, the bonding roller 51 and the auxiliary rollers 42 are rotated in a counterclockwise direction in FIG. 1, and the first sheet conveying roller 31 and the auxiliary rollers 32 are rotated in a clockwise direction in FIG. 1. Rotation of the cylinder part 21 is performed by driving a belt wound around the cylinder part 21 in a circumferential direction. The first sheet conveying roller 31 is a sheet conveying part for conveying a first sheet member 91, which is continuous sheet formed of nonwoven fabric or the like, to a vicinity of a lowermost portion of the cylinder part 21. The first applying part 61 is located above the plurality of auxiliary rollers 32, and applies adhesive onto the first sheet member 91.

The second sheet conveying roller 41 is a sheet conveying part for conveying a second sheet member 92, which is continuous sheet formed of nonwoven fabric or the like, to the vicinity of the lowermost portion of the cylinder part 21. The second applying part 62 is located above the plurality of auxiliary rollers 42, and applies adhesive onto the second sheet member 92. The cylinder part 21 supplies particles of high-absorbent resin (hereinafter, simply referred to as "particles") onto the first sheet member 91 in the vicinity of the lowermost portion. The bonding roller 51 is provided beside the first sheet conveying roller 31. The bonding roller 51 is a sheet bonding part for bonding the first sheet member 91 and the second sheet member 92 with each other by overlapping the first sheet member 91 and the second sheet member 92 with each other and sandwiching them between the first sheet conveying roller 31 and the bonding roller 51.

A cylindrical exhaust part 24 is provided above the cylinder part 21, and an upper opening of the exhaust part 24 is covered with a pouched filter 241 formed of nonwoven fabric or the like. A first cover part 221 which covers a portion of the outer side surface 211 of the cylinder part 21 and a second cover part 222 which covers another portion of the outer side surface 211 are provided around the cylinder part 21. The first cover part 221 spreads from the vicinity of the lowermost portion of the cylinder part 21 to the exhaust part 24 along an opposite direction of the rotation direction of the cylinder part 21 (i.e., toward the posterior side in the rotation direction (that is, in the clockwise direction in FIG. 1)), to cover the outer side surface 211 in the left side of the cylinder part 21. The second cover part 222 spreads from a vicinity of a right end portion of the cylinder part 21 to the exhaust part 24 along the rotation direction of the cylinder part 21 (i.e., in the counterclockwise direction in FIG. 1), to cover the outer side surface 211 in the right side of the cylinder part 21. In the outer side surface 211 of the cylinder part 21, a region between the lower end of the first cover part 221 and the lower end of the second cover part 222, that is a region which is not covered with the first cover part 221 and the second cover part 222 in the lower side of the cylinder part 21, is an after-mentioned particle supply region 210. The first cover part 221 spreads from the particle supply region 210 in the clockwise direction, and the second cover part 222 spreads from the particle supply region 210 in the counterclockwise direction.

Figure 2:
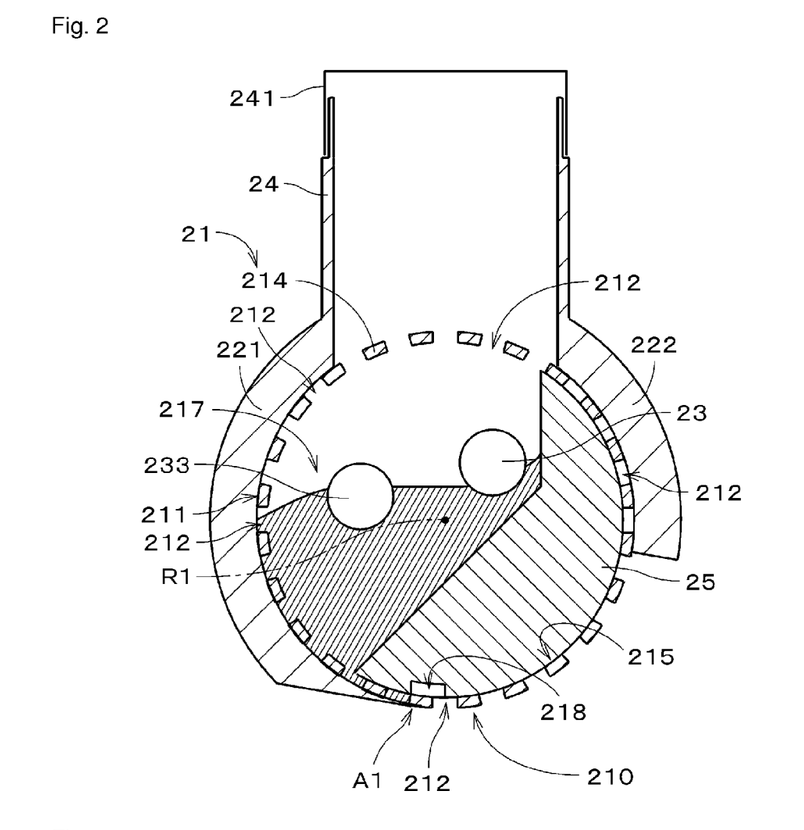
FIG. 2 is a cross-sectional view of a vicinity of a cylinder part.
Figure 3:
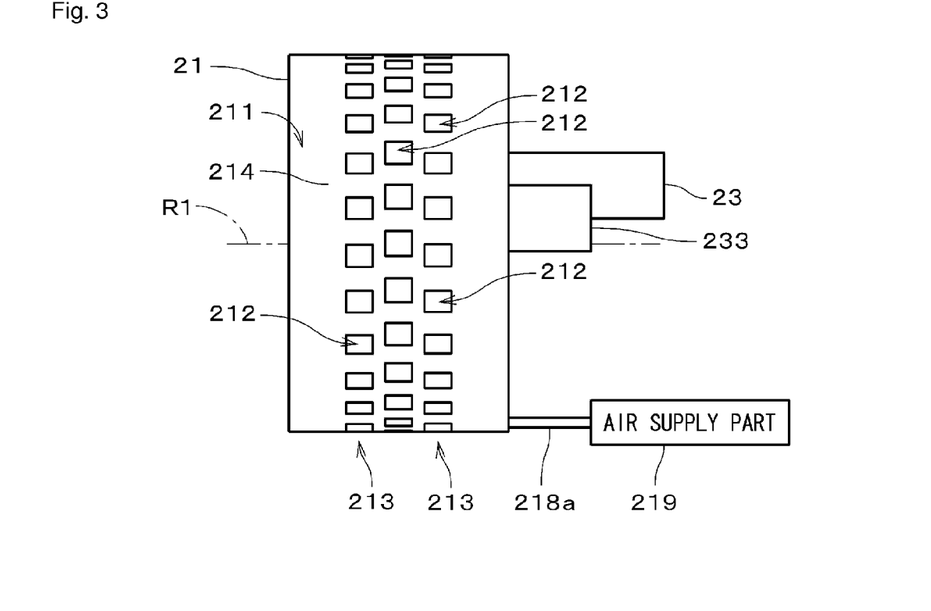
FIG. 3 is a front view of the cylinder part.

FIG. 2 is an enlarged cross-sectional view showing the vicinity of the cylinder part 21, and shows a cross section which is orthogonal to the rotation axis R1. In FIG. 2, constituents on the near side of the cross section are also drawn. FIG. 3 is a view showing the outer side surface 211 of the cylinder part 21, and in FIG. 3, an appearance of the outer side surface 211 of the cylinder part 21 which is observed along a direction orthogonal to the rotation axis R1 is shown. In FIG. 3, the first cover part 221 and the second cover part 222 are omitted.

As shown in FIGS. 2 and 3, the cylinder part 21 has a plurality of through-holes 212 which are holes passing through its side wall 214. The plurality of through-holes 212 are arranged at regular intervals in the circumferential direction around the rotation axis R1 with respect to each of a plurality of positions in the axial direction. When the plurality of through-holes 212 which are arranged in the circumferential direction at the same position in the axial direction are referred to as a through-hole row 213, three through-hole rows 213 are provided in the cylinder part 21 as shown in FIG. 3. In the present embodiment, the shape of each through-hole 212 is generally rectangular, however the through-holes 212 may have a various shape (for example, generally circular shape). In the cylinder part 21, one, two, four or more through-hole rows 213 may be provided. In each through-hole row 213, the through-holes 212 are not necessarily arranged at regular intervals.

As shown in FIG. 2, an isolation part 25 which covers a portion of an inner side surface 215 of the side wall 214 of the cylinder part 21 is provided in the internal space of the cylinder part 21. The isolation part 25 is provided in the right portion of the internal space in FIG. 2 and covers the right portion of the inner side surface 215 from the vicinity of the lowermost portion of the cylinder part 21 to the vicinity of the uppermost portion. An outer surface of the isolation part 25 (i.e., a surface facing the inner side surface 215 of the cylinder part 21) faces a lower end portion of the first cover part 221, the whole particle supply region 210 and the whole second cover part 222. An upper portion of an inner surface of the isolation part 25 is in almost parallel with the vertical direction (i.e., direction of gravitational force), and a lower portion of the inner surface is inclined toward the lower left in FIG. 2. In other words, the lower portion of the inner surface of the isolation part 25 goes downward in the vertical direction while linearly approaching the lower portion of the first cover part 221. The lower portion of the inner surface of the isolation part 25 may be a curved surface which is convex upward or downward.

In the cylinder part 21, a portion of the internal space where the isolation part 25 doesn't exist is a particle storage space 217 which stores particles of high-absorbent resin. In FIG. 2, regions of the particles are densely hatched. As mentioned previously, the lower portion of the inner surface of the isolation part 25 goes downward while approaching the lower portion of the first cover part 221. Thus, the particles in the particle storage space 217 move along the inner surface of the isolation part 25 toward the inner side surface 215 of the cylinder part 21. The isolation part 25 is provided across almost the entire width of the inner side surface 215 of the cylinder part 21 in the axial direction, so that through-holes 212 in a region of the inner side surface 215 which is covered with the isolation part 25 are isolated from the particle storage space 217. Thus, also in the particle supply region 210, through-holes 212 are isolated from the particle storage space 217.

As shown in FIGS. 2 and 3, the absorbent sheet manufacturing apparatus 1 has a particle replenishment part 23 provided to the right side of the cylinder part 21 in FIG. 3. The particle replenishment part 23 is a screw feeder which has a screw therein, and replenishes particles into the particle storage space 217 of the cylinder part 21 from one end portion (right end portion in FIG. 3) of the cylinder part 21 in the axial direction. A light-receiving, ultrasonic or contact level sensor 233 is provided in the particle storage space 217. When the amount of particles stored in the particle storage space 217 becomes equal to or less than a certain level, replenishment of particles is performed. When particles are replenished into the particle storage space 217 shown in FIG. 2, air in the particle storage space 217 is exhausted mainly through the exhaust part 24. Even if particles go out into the exhaust part 24 from the cylinder part 21, the particles are prevented by the filter 241 from going outside of the absorbent sheet manufacturing apparatus 1.

In the absorbent sheet manufacturing apparatus 1, the cylinder part 21 is rotated at a high speed around the rotation axis R1, so that particles in the particle storage space 217 are filled into through-holes 212, which face particles stored in the particle storage space 217, out of the plurality of through-holes 212 in the cylinder part 21. Until each through-hole 212 filled with particles reaches the particle supply region 210 provided in the lower portion of the cylinder part 21, the outer end of the through-hole 212 is closed (blocked) with the first cover part 221 (that is, the through-hole 212 is covered on the outer side surface 211). In addition, the through-hole 212 is moved to a position where the through-hole 212 faces the isolation part 25, and therefore the particles in the through-hole 212 is isolated (separated) from particles in the particle storage space 217. Then, when each through-hole 212 pass the particle supply region 210 beyond an edge of the first cover part 221 in the vicinity of the lowermost portion of the cylinder part 21, that is, beyond an anterior edge of the first cover part 221 in the rotation direction of the cylinder part 21, particles filled in the through-hole 212 are ejected out of the cylinder part 21.

Specifically, ejection of particles is started at the moment (an anterior portion of) the through-hole 212 has passed over the above edge of the first cover part 221. In the following description, a position of the above edge is referred to as an "ejection start position A1". The ejection start position A1 lies posterior to (upstream of) the lowermost portion of the cylinder part 21 in the rotation direction of the cylinder part 21 and is positioned in the vicinity of the lowermost portion of the cylinder part 21. As mentioned previously, the cylinder part 21 is rotated at a high speed, and particles are sequentially ejected from the plurality of through-holes 212 almost along a tangent line of the outer side surface 211 at the ejection start position A1.

The isolation part 25 has an air supply path 218 for conducting air into a through-hole 212, which faces (overlaps with) the ejection start position A1, at a position near (close to) and anterior to the ejection start position A1 in the rotation direction of the cylinder part 21 (i.e., at a posterior end portion of the particle supply region 210 in the above rotation direction). The air supply path 218 extends in the axial direction of the cylinder part 21 and is connected to an air supply part 219 through a pipe 218a as shown in FIG. 3. The air supply part 219 is configured to forcedly supply air into the air supply path 218.

Each through-hole 212 which has ejected particles passes through the particle supply region 210 while its inner end is closed by the isolation part 25 so that the through-hole 212 is isolated from the particle storage space 217 as shown in FIG. 2. Subsequently, the through-hole 212 is moved to the upper portion of the cylinder part 21 with its inner and outer ends closed by the isolation part 25 and the second cover part 222. Then, at a position where the through-hole 212 faces the exhaust part 24, the inner and outer ends of the through-hole 212 are opened, so that the through-hole 212 comes into communication with the particle storage space 217 and the exhaust part 24.

Figure 4:
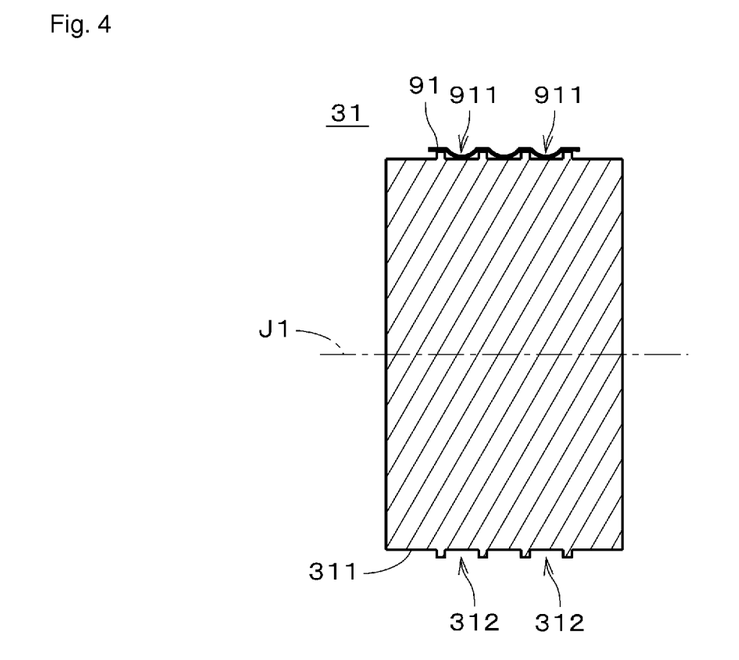
FIG. 4 is a cross-sectional view of a first sheet conveying roller.

FIG. 4 is a cross-sectional view of the first sheet conveying roller 31 and shows a cross section of the first sheet conveying roller 31 taken along a plane including the rotation axis R1 of the cylinder part 21 in FIG. 1 and the first central axis J1 of the first sheet conveying roller 31. The first sheet conveying roller 31 has an outer side surface 311 which is a generally cylindrical surface around the first central axis J1, and an annular groove 312 along a circumferential direction around the first central axis J1 is formed on the outer side surface 311 with respect to each of the plurality of positions in the axial direction. The annular grooves 312 are located at the same positions in the axial direction as the positions of the through-hole rows 213 in the cylinder part 21.

The first sheet member 91 is led to the first sheet conveying roller 31 through the plurality of auxiliary rollers 32 (see FIG. 1). At this time, adhesive is applied by the first applying part 61 onto only a plurality of strip-like regions (or linear regions) on the first sheet member 91 which are overlapped with the plurality of annular grooves 312, respectively. Positions of the plurality of strip-like regions (hereinafter referred to as "adhesive-applied regions") are identical to the positions of the plurality of through-hole rows 213 in the cylinder part 21 and the positions of the plurality of annular grooves 312 with respect to the axial direction. Under the ejection start position A1 (see FIG. 2) of the particle supply region 210, the first sheet member 91 is conveyed by the first sheet conveying roller 31 in the same direction as a moving direction of the outer side surface 211 of the cylinder part 21 (i.e., rightward in FIG. 1). From the cylinder part 21, particles are ejected toward the plurality of adhesive-applied regions on the first sheet member 91 to be held on the first sheet member 91.

In the first sheet conveying roller 31, a diameter of the outer side surface 311 is comparatively-large, and also the first sheet member 91 is stretched along the outer side surface 311 at a certain tension. Therefore, a portion 911 of the first sheet member 91 corresponding to each annular groove 312 becomes a shape depressed toward the bottom of the annular groove 312. In other words, groove portions 911 corresponding to the annular grooves 312 are formed on the first sheet member 91. As mentioned previously, the positions of the annular grooves 312 in the first sheet conveying roller 31 are same as the positions of the through-hole rows 213 with respect to the axial direction. Thus, most particles ejected from each through-hole 212 go toward the groove portion 911 to be collected in the groove portion 911. At this time, even if particles bounce from the first sheet member 91 in the groove portions 911, scattering of particles to the outside of the groove portions 911 is suppressed (reduced) by side walls of the groove portions 911. In addition, since the above adhesive-applied regions on the first sheet member 91 are positioned at the groove portions 911, particles are easily caught in the groove portions 911.

Figure 5:
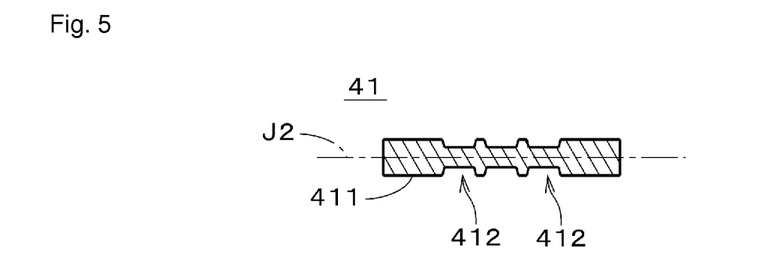
FIG. 5 is a cross-sectional view of a second sheet conveying roller.

FIG. 5 is a cross-sectional view of the second sheet conveying roller 41 and shows a cross section of the second sheet conveying roller 41 taken along a plane including the second central axis J2 of the second sheet conveying roller 41 in FIG. 1. The second sheet conveying roller 41 has an outer side surface 411 which is a generally cylindrical surface around the second central axis J2, and an annular groove 412 along a circumferential direction around the second central axis J2 is formed on the outer side surface 411 with respect to each of the plurality of positions in the axial direction. The plurality of annular grooves 412 are located at the same positions in the axial direction as the positions of the plurality of through-hole rows 213 in the cylinder part 21 and the positions of the plurality of annular grooves 312 in the first sheet conveying roller 31.

The second sheet member 92 is led to the second sheet conveying roller 41 through the plurality of auxiliary rollers 42 (see FIG. 1). At this time, adhesive is applied by the second applying part 62 onto only a plurality of strip-like (or linear) adhesive-applied regions on the second sheet member 92 which are overlapped with the plurality of annular grooves 412. Positions of the plurality of adhesive-applied regions are identical to the positions of the plurality of through-hole rows 213 in the cylinder part 21 and the positions of the plurality of annular grooves 312 in the first sheet conveying roller 31 with respect to the axial direction. Some of particles ejected from each through-hole 212 of the cylinder part 21 bounce from the first sheet member 91 in the groove portion 911 (see FIG. 4) to go toward the second sheet conveying roller 41, and others go from the through-hole 212 of the cylinder part 21 to the second sheet conveying roller 41 directly.

Figure 6:
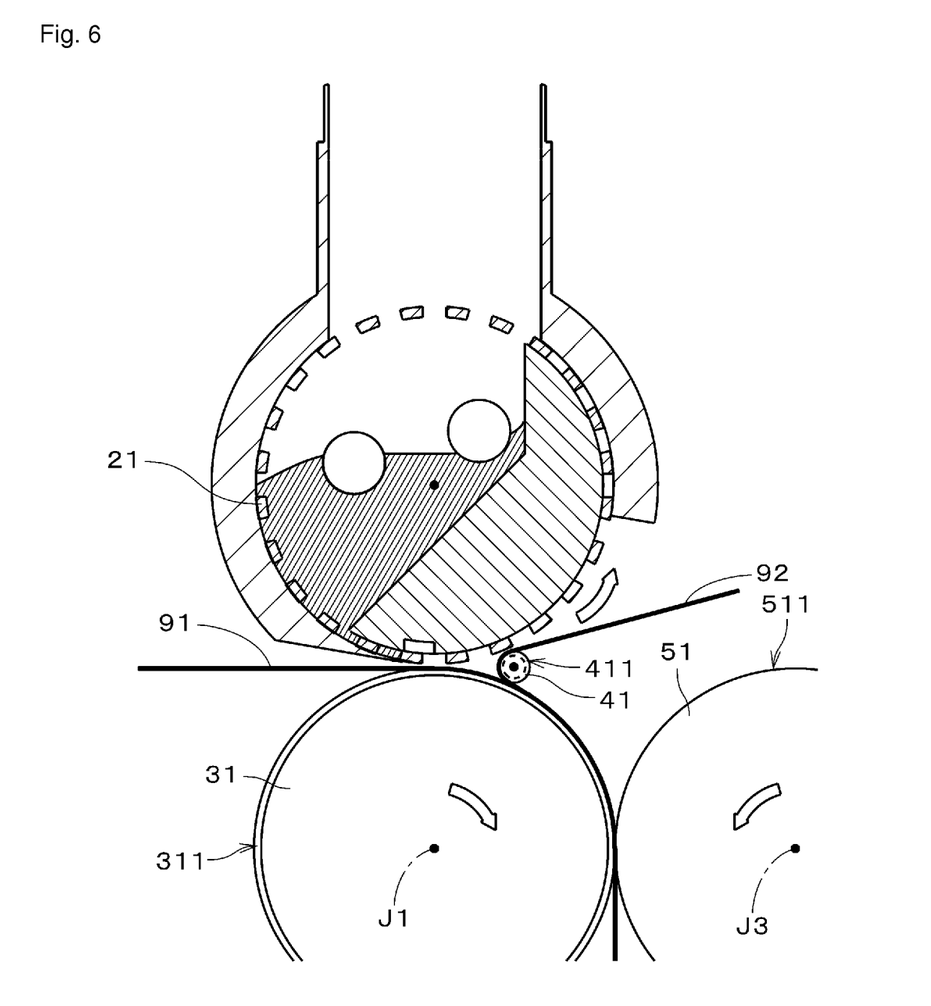
FIG. 6 is a view showing the vicinity of the cylinder part.

As mentioned previously, the positions of the annular grooves 412 in the second sheet conveying roller 41 are same as the positions of the through-hole rows 213 and the positions of the annular grooves 312 with respect to the axial direction, and the particles heading to the second sheet conveying roller 41 collide with portions of the second sheet member 92 lying right above the annular grooves 412 (i.e., portions at which the back surface is not in contact with any substance). As a result, the impact is absorbed and the particles are collected in the groove portions 911 of the first sheet member 91. As shown in FIG. 6, the second sheet member 92 is conveyed along the outer side surface 411 of the second sheet conveying roller 41, and (a portion of) the second sheet member 92 is placed (stacked) on (a portion of) the first sheet member 91 which has passed under the lowermost portion of the cylinder part 21.

Figure 7:
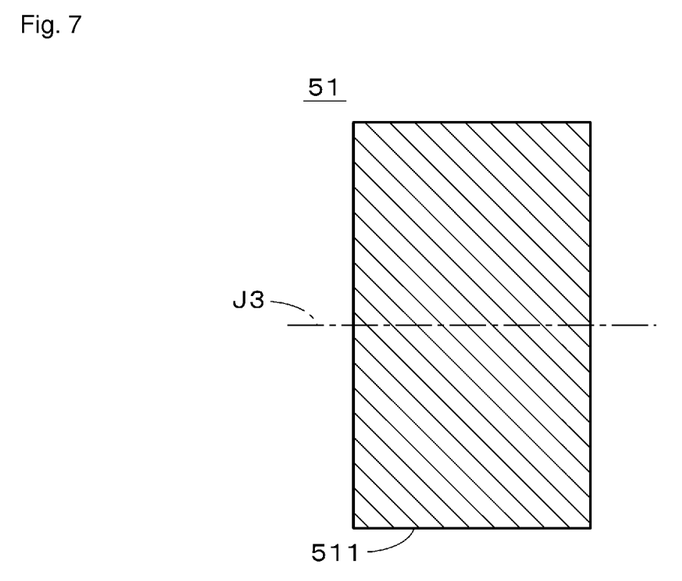
FIG. 7 is a cross-sectional view of a bonding roller.

FIG. 7 is a cross-sectional view of the bonding roller 51 and shows a cross section of the bonding roller 51 taken along a plane including the third central axis J3 of the bonding roller 51 in FIG. 1. The bonding roller 51 has an outer side surface 511 which is a cylindrical surface around the third central axis J3, and the outer side surface 511 is a smooth surface. As shown in FIG. 6, the first sheet member 91 and the second sheet member 92 overlapped with each other are placed (sandwiched) between the outer side surface 311 of the first sheet conveying roller 31 and the outer side surface 511 of the bonding roller 51. The both (or one) of the first sheet conveying roller 31 and the bonding roller 51 are provided with heaters, and regions of the first sheet member 91 and the second sheet member 92 which come into contact with convex portions lying at both sides of each annular groove 312 (see FIG. 4) on the outer side surface 311 of the first sheet conveying roller 31 are heat-sealed, so that the first sheet member 91 and the second sheet member 92 are bonded with each other.

Figure 8:
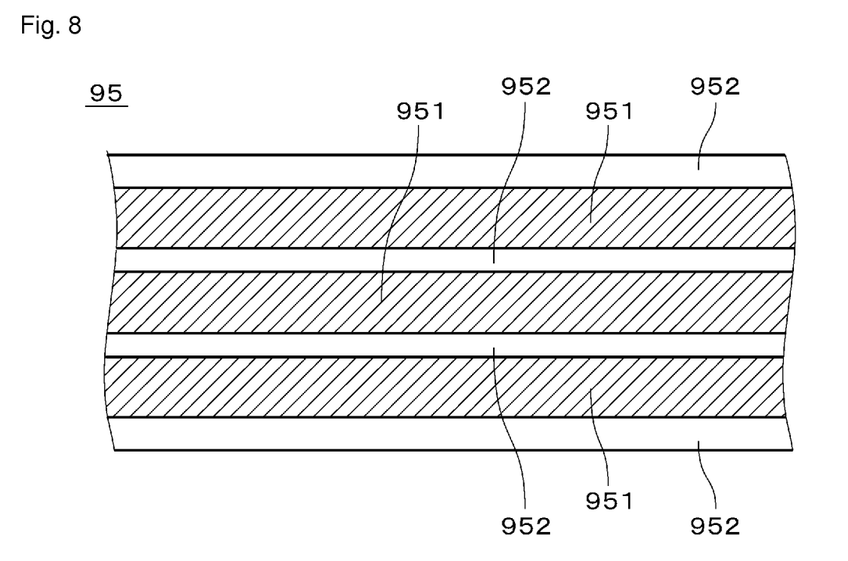
FIG. 8 is a plain view of an absorbent sheet.

Therefore, as shown in FIG. 8, an absorbent sheet 95 where a plurality of particle existence regions 951 and a plurality of particle non-existence regions 952 are alternately arranged in the width direction is formed. The plurality of particle existence regions 951 are strip-like (or linear) regions on each of which particles of high-absorbent resin are applied, and the plurality of particle non-existence regions 952 are strip-like (or linear) regions where particles don't exist essentially and the first sheet member 91 and the second sheet member 92 are bonded with each other. In other words, the plurality of particle existence regions 951 are provided in a stripe pattern in the absorbent sheet 95. In FIG. 8, hatching lines are drawn in the particle existence regions 951.

As described above, in the absorbent sheet manufacturing apparatus 1, the generally cylindrical cylinder part 21 having the plurality of through-holes 212 arranged in the circumferential direction is provided, and particles of high-absorbent resin are filled into each through-hole 212 from the particle storage space 217 in the inside of the rotating cylinder part 21. In the particle supply region 210, the inner side surface 215 of the cylinder part 21 is covered with the isolation part 25, and ejection of particles from the through-hole 212 is performed while the through-hole 212 filled with particles is isolated from the particle storage space 217 (i.e., the through-hole 212 isn't in communication with the particle storage space 217). As above, only particles filled in each through-hole 212 are ejected, and therefore a desired amount of particles can be easily supplied from the through-hole 212. Since the amounts of particles filled in respective through-holes 212 are almost constant, the amounts of particles ejected from the plurality of through-holes 212 can be constant.

In the absorbent sheet manufacturing apparatus 1, the air supply path 218 is provided at the posterior end portion of the particle supply region 210 in the rotation direction, and air is conducted into the through-hole 212 passing the ejection start position A1 and moving to the particle supply region 210. Therefore, particles filled in the through-hole 212 easily fall out from the through-hole 212. As a result, particles can be ejected smoothly from the through-hole 212. By the air supply part 219 forcedly supplying air into the air supply path 218, particles can be ejected more smoothly from the through-hole 212.

As mentioned previously, particles are supplied by the particle replenishment part 23 into the particle storage space 217 from one end portion of the cylinder part 21 in the axial direction. This makes it possible to easily perform replenishment of particles into the particle storage space 217 without being influenced by the rotation of the cylinder part 21.

Figure 9:
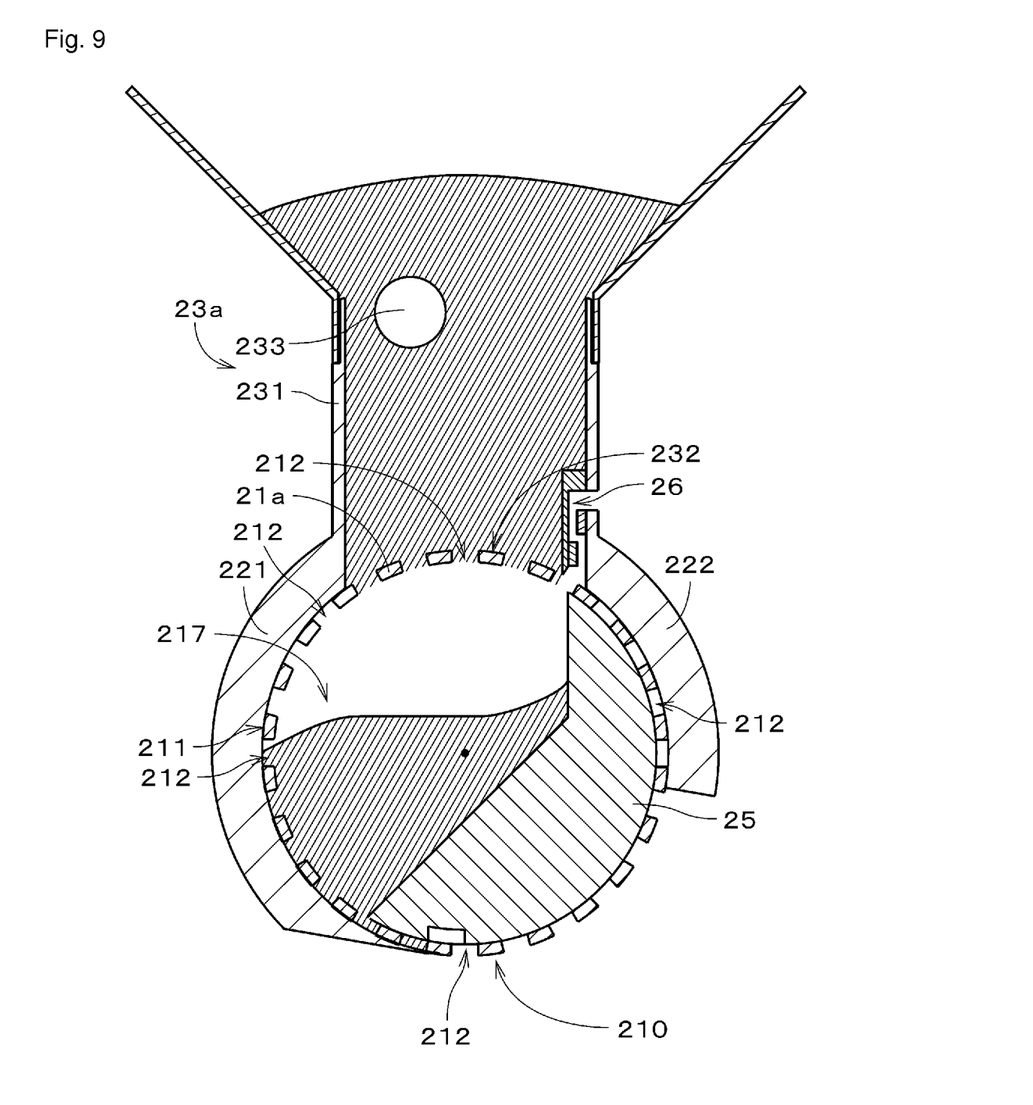
FIG. 9 is a view showing a vicinity of a cylinder part in an absorbent sheet manufacturing apparatus in accordance with a second preferred embodiment.
Figure 10:
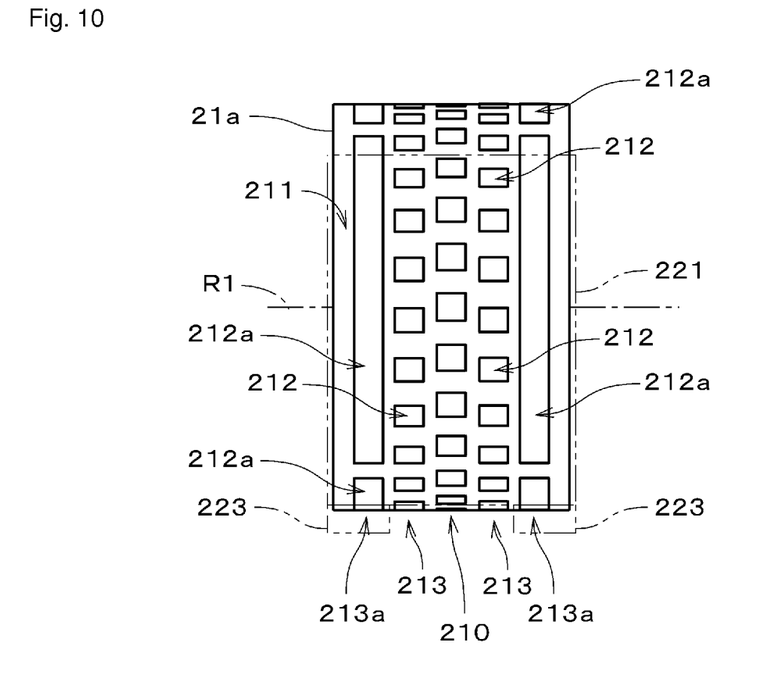
FIG. 10 is a front view of the cylinder part.

Next, discussion will be made on an absorbent sheet manufacturing apparatus in accordance with a second preferred embodiment of the present invention. FIG. 9 is a view showing a vicinity of a cylinder part 21a in an absorbent sheet manufacturing apparatus in accordance with the second preferred embodiment, and FIG. 9 corresponds to FIG. 2 described above. FIG. 10 is a view showing an outer side surface 211 of the cylinder part 21a, and FIG. 10 corresponds to FIG. 3 described above. In FIG. 10, the first cover part 221 is drawn by chain double-dashed lines in order to facilitate understanding of the drawing. In the absorbent sheet manufacturing apparatus in accordance with the second preferred embodiment, as shown in FIG. 9, a particle replenishment part 23a is provided above the cylinder part 21a as substitute for the particle replenishment part 23 (see FIGS. 2 and 3), and a communication part 26 is provided on the right side of the particle replenishment part 23a in FIG. 9. In addition, as shown in FIG. 10, a plurality of auxiliary through-holes 212a are provided to each side of the three through-hole rows 213 in the cylinder part 21a (so as to sandwich the three through-hole rows 213 therebetween). The other constituent elements are almost same as those of the absorbent sheet manufacturing apparatus 1 shown in FIG. 1, and the same elements are denoted by the same reference signs in the following description.

As shown in FIG. 10, two auxiliary through-hole rows 213a are provided to both sides of the three through-hole rows 213 in the axial direction, respectively so as to be adjacent to these through-hole rows 213 in the cylinder part 21a. Each auxiliary through-hole row 213a has three auxiliary through-holes 212a each extending in a circumferential direction around the rotation axis R1, and the three auxiliary through-holes 212a are arranged in the circumferential direction at regular intervals. In the present embodiment, each auxiliary through-hole 212a is adjacent to eight through-holes 212 continuously arranged in the circumferential direction. On the outer side surface 211 of the cylinder part 21a, the auxiliary through-holes 212a are covered with the first cover part 221 and the second cover part 222 (see FIG. 9). In a region (i.e., particle supply region 210) between the lower end of the first cover part 221 and the lower end of the second cover part 222, the auxiliary through-holes 212a are covered on the outer side surface 211 with a third cover part 223 which lies to each side of the three through-hole rows 213 to connect the first cover part 221 to the second cover part 222. In other words, each auxiliary through-hole 212a is covered on the outer side surface 211 of the cylinder part 21a (from the outer side surface's side) in a (whole) region other than an aftermentioned particle replenishment opening 232.

As shown in FIG. 9, the particle replenishment part 23a has a particle tank 231 which is located above the cylinder part 21a and which stores the particles of high-absorbent resin. The particle tank 231 extends almost in parallel with the vertical direction, and a particle replenishment opening 232 facing the outer side surface 211 of the cylinder part 21a is provided to a lower end of the particle tank 231. In the absorbent sheet manufacturing apparatus in accordance with the second preferred embodiment, particles in the particle tank 231 of the particle replenishment part 23a fall by gravity into the particle storage space 217 through the plurality of through-holes 212 and the plurality of auxiliary through-holes 212a (see FIG. 10) in the cylinder part 21a, so that particles are replenished into the particle storage space 217. A level sensor 233 is provided in the particle tank 231. When the amount of particles stored in the particle tank 231 becomes equal to or less than a certain level, particles are replenished into the particle tank 231.

The communication part 26 is adjacent to the right side (i.e., a posterior side in the rotation direction of the cylinder part 21a) of the particle replenishment opening 232 in FIG. 9, and is provided across almost the entire extent where the three through-hole rows 213 and the two auxiliary through-hole rows 213a are arranged in the axial direction of the cylinder part 21a. A through-hole 212 out of the plurality of through-holes 212 and an auxiliary through-hole 212a out of the plurality of auxiliary through-holes 212a, both of which face a posterior edge of the particle replenishment opening 232 (i.e., a posterior end in the rotation direction of the cylinder part 21a) in the cylinder part 21a, are brought into communication with external space by the communication part 26.

In the absorbent sheet manufacturing apparatus in accordance with the second preferred embodiment, the cylinder part 21a is rotated at a high speed, and particles of high-absorbent resin are filled into each through-hole 212 from the particle storage space 217 in the inside of the cylinder part 21a, in the same manner as the above absorbent sheet manufacturing apparatus 1. Then, in the particle supply region 210, ejection of particles from the through-hole 212 is performed while the through-hole 212 filled with particles is isolated from the particle storage space 217 by the isolation part 25. It is therefore possible to easily supply a desired amount of particles from each through-hole 212. In addition, the amounts of particles ejected from the plurality of through-holes 212 can be constant.

In the absorbent sheet manufacturing apparatus in accordance with the second preferred embodiment, the particle replenishment part 23a storing particles is provided above the cylinder part 21a, and particles are filled from the particle replenishment part 23a into the particle storage space 217 of the cylinder part 21a. In the particle replenishment part 23a, a large amount of particles can be stored in the particle tank 231, and therefore stable replenishment of particles into the particle storage space 217 can be easily achieved. Since the auxiliary through-holes 212a are provided in the cylinder part 21a, replenishment of particles from the particle replenishment part 23a into the particle storage space 217 can be performed promptly. As mentioned previously, the auxiliary through-holes 212a of the cylinder part 21a are covered on the outer side surface 211 of the cylinder part 21a in a region other than the particle replenishment opening 232. Thus, particles aren't ejected from any auxiliary through-hole 212a onto the first sheet member 91 (see FIG. 1) or the like.

As mentioned previously, the communication part 26 is provided in the absorbent sheet manufacturing apparatus, and the through-hole 212 and auxiliary through-hole 212a which face the posterior edge of the particle replenishment opening 232 (which face the particle replenishment opening 232 at the posterior edge) are brought into communication with the external space through the communication part 26. Thus, when particles are replenished from the particle replenishment part 23a into the particle storage space 217, air in the particle storage space 217 can easily escape to the external space through the through-hole 212 and auxiliary through-hole 212a facing the communication part 26. As a result, replenishment of particles into the particle storage space 217 can be performed more easily.

Though the preferred embodiments of the present invention have been discussed above, the present invention is not limited to the above-discussed preferred embodiments, but allows various variations.

For example, in the absorbent sheet manufacturing apparatus 1 in accordance with the first preferred embodiment, as substitute for the screw feeder, an air feeder for conveying material with compressed air may be utilized as the particle replenishment part 23. If particles can be ejected smoothly from the through-hole 212 at the ejection start position A1, there may be a case where air supply from the air supply part 219 to the air supply path 218 isn't performed and the air supply path 218 is omitted.

In the cylinder part 21a of the absorbent sheet manufacturing apparatus in accordance with the second preferred embodiment, if the particle storage space 217 can be supplied with sufficient particles, a plurality of auxiliary through-holes 212a or one auxiliary through-hole 212a may be provided to only one side of the plurality of through-hole rows 213 in the axial direction. In the cylinder part 21, 21a, only one through-hole row 213 may be provided.

In the above preferred embodiment, discussion has been made on the manufacture (production) of the absorbent sheets 95 where the striped particle existence regions 951 are set, however, absorbent sheets having point-like (dotted) particle existence regions may be formed by decreasing the rotation speed of the cylinder part 21, 21a or increasing spaces between adjacent through-holes 212 in the circumferential direction in the cylinder part 21, 21a.

The above cylinder part 21, 21a, first sheet conveying roller 31, first cover part 221 and isolation part 25 which function as a particle supplying apparatus for supplying particles of high-absorbent resin onto a sheet member may be utilized (combined) in various apparatuses other than the absorbent sheet manufacturing apparatus. For example, there may be a case where a sheet member whose upper surface is supplied with pulp fibers or the like is conveyed by the first sheet conveying roller 31 and particles of high-absorbent resin are supplied onto the pulp fibers by the cylinder part 21, 21a. In this case, a desired amount of particles can be mixed with the pulp fibers uniformly.

In the above particle supplying apparatus, particles of absorbent material are supplied such as crosslinked partially neutralized polyacrylic acid, hydrolyzed starch-acrylic acid graft polymer, saponified vinyl acetate-acrylic ester copolymer, hydrolyzed acrylonitrile copolymer, crosslinked acrylonitrile copolymer, hydrolyzed acrylamide copolymer, crosslinked acrylamide copolymer, crosslinked cationic monomers, or crosslinked polyamino acid. The particle supplying apparatus may be utilized as an apparatus for supplying particles of deodorant material such as activated carbon, silica, alumina, zeolite, ion-exchange resin, or molecular sieve onto a sheet member. In this case, a sheet article manufacturing apparatus having the above particle supplying apparatus manufactures a deodorant sheet which is a sheet article for an absorbent article such as a disposable diaper or absorbent pad for light incontinence.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 Absorbent sheet manufacturing apparatus
21, 21a Cylinder part
23, 23a Particle replenishment part
25 Isolation part
26 Communication part
31 First sheet conveying roller
91 First sheet member
95 Absorbent sheet
210 Particle supply region
211, 311 Outer side surface
212 Through-hole
212a Auxiliary through-hole
215 Inner side surface
217 Particle storage space
218 Air supply path
219 Air supply part
221 First cover part
232 Particle replenishment opening
R1 Rotation axis

The invention claimed is:

1. A particle supplying apparatus for supplying particles of absorbent material or deodorant material onto a sheet member, comprising:
   a cylinder part which is a generally cylindrical member around a rotation axis along a horizontal direction, a portion of an internal space of said cylinder part being a particle storage space which stores particles of absorbent material or deodorant material, said cylinder part having a plurality of through-holes arranged in a circumferential direction and being rotated around said rotation axis so that particles are filled into a through-hole out of said plurality of through-holes which faces particles stored in said particle storage space, to eject particles filled in said through-hole outward at a particle supply region provided in a lower portion thereof;
   a sheet conveying part for conveying a sheet member in a direction under said particle supply region, said direction being same as a moving direction of an outer side surface of said cylinder part;
   a cover part which spreads from said particle supply region along an opposite direction of a rotation direction of said cylinder part to cover a portion of said outer side surface of said cylinder part and close an outer end of said through-hole filled with particles; and
   an isolation part which covers a portion of an inner side surface of said cylinder part to isolate a through-hole in said particle supply region from said particle storage space.

2. The particle supplying apparatus according to claim 1, wherein
   said isolation part has an air supply path for conducting air into a through-hole of said cylinder part at a posterior end portion of said particle supply region in said rotation direction.

3. The particle supplying apparatus according to claim 2, further comprising
   an air supply part for forcedly supplying air into said air supply path.

4. The particle supplying apparatus according to claim 3, further comprising
   a particle replenishment part for replenishing particles into said particle storage space from one end portion of said cylinder part in an axial direction thereof.

5. The particle supplying apparatus according to claim 2, further comprising
   a particle replenishment part for replenishing particles into said particle storage space from one end portion of said cylinder part in an axial direction thereof.

6. The particle supplying apparatus according to claim 2, wherein
   said cylinder part has an auxiliary through-hole which is adjacent to said plurality of through holes in an axial direction thereof and which extends in a circumferential direction thereof,
   said particle supplying apparatus further comprises a particle replenishment part which is located above said cylinder part and which stores particles of absorbent material or deodorant material, for replenishing particles into said particle storage space from a particle replenishment opening through said plurality of through-holes and said auxiliary through-hole, said particle replenishment opening facing said outer side surface of said cylinder part, and
   said auxiliary through-hole is covered on said outer side surface of said cylinder part in a region other than said particle replenishment opening.

7. The particle supplying apparatus according to claim 3, wherein
   said cylinder part has an auxiliary through-hole which is adjacent to said plurality of through-holes in an axial direction thereof and which extends in a circumferential direction thereof,
   said particle supplying apparatus further comprises a particle replenishment part which is located above said cylinder part and which stores particles of absorbent material or deodorant material, for replenishing particles into said particle storage space from a particle replenishment opening through said plurality of through-holes and said auxiliary through-hole, said particle replenishment opening facing said outer side surface of said cylinder part, and
   said auxiliary through-hole is covered on said outer side surface of said cylinder part in a region other than said particle replenishment opening.

8. The particle supplying apparatus according to claim 1, further comprising
   a particle replenishment part for replenishing particles into said particle storage space from one end portion of said cylinder part in an axial direction thereof.

9. The particle supplying apparatus according to claim 1, wherein
   said cylinder part has an auxiliary through-hole which is adjacent to said plurality of through-holes in an axial direction thereof and which extends in a circumferential direction thereof,
   said particle supplying apparatus further comprises a particle replenishment part which is located above said cylinder part and which stores particles of absorbent material or deodorant material, for replenishing particles into said particle storage space from a particle replenishment opening through said plurality of through-holes and said auxiliary through-hole, said particle replenishment opening facing said outer side surface of said cylinder part, and
   said auxiliary through-hole is covered on said outer side surface of said cylinder part in a region other than said particle replenishment opening.

10. The particle supplying apparatus according to claim 9, further comprising
    a communication part which is located adjacent and posterior to said particle replenishment opening in said rotation direction, a through-hole out of said plurality of through-holes being in communication with external space through said communication part, said through-hole facing a posterior edge of said particle replenishment opening.

11. A sheet article manufacturing apparatus for manufacturing a sheet article for an absorbent article, comprising:
    a particle supplying apparatus according to claim 1;
    another sheet conveying part for conveying another sheet member; and
    a sheet bonding part for placing said another sheet member on said sheet member which has been supplied with particles by said particle supplying apparatus, to bond said another sheet member on said sheet member.

12. A sheet article manufacturing apparatus for manufacturing a sheet article for an absorbent article, comprising:
    a particle supplying apparatus according to claim 2;
    another sheet conveying part for conveying another sheet member; and
    a sheet bonding part for placing said another sheet member on said sheet member which has been supplied with particles by said particle supplying apparatus, to bond said another sheet member on said sheet member.

13. A sheet article manufacturing apparatus for manufacturing a sheet article for an absorbent article, comprising:
    a particle supplying apparatus according to claim 3;
    another sheet conveying part for conveying another sheet member; and
    a sheet bonding part for placing said another sheet member on said sheet member which has been supplied with particles by said particle supplying apparatus, to bond said another sheet member on said sheet member.

14. A sheet article manufacturing apparatus for manufacturing a sheet article for an absorbent article, comprising:
    a particle supplying apparatus according to claim 8;
    another sheet conveying part for conveying another sheet member; and
    a sheet bonding part for placing said another sheet member on said sheet member which has been supplied with particles by said particle supplying apparatus, to bond said another sheet member on said sheet member.

15. A sheet article manufacturing apparatus for manufacturing a sheet article for an absorbent article, comprising:
    a particle supplying apparatus according to claim 9;
    another sheet conveying part for conveying another sheet member; and
    a sheet bonding part for placing said another sheet member on said sheet member which has been supplied with particles by said particle supplying apparatus, to bond said another sheet member on said sheet member.

16. A sheet article manufacturing apparatus for manufacturing a sheet article for an absorbent article, comprising:
    a particle supplying apparatus according to claim 10;
    another sheet conveying part for conveying another sheet member; and
    a sheet bonding part for placing said another sheet member on said sheet member which has been supplied with particles by said particle supplying apparatus, to bond said another sheet member on said sheet member.

* * * * *